United States Patent
Cottais et al.

(10) Patent No.: US 7,444,855 B2
(45) Date of Patent: Nov. 4, 2008

(54) ORTHOGONAL RHEOMETER

(75) Inventors: Frédéric Cottais, Lezoux (FR); Patrice Monnereau, Culhat (FR); Daniel Meyer, Chamalieres (FR)

(73) Assignee: Michelin Recherche et Technique, S.A., Granges-Paccot (CH)

( * ) Notice: Subject to any disclaimer, the term of this patent is extended or adjusted under 35 U.S.C. 154(b) by 0 days.

(21) Appl. No.: 11/811,956

(22) Filed: Jun. 11, 2007

(65) Prior Publication Data

US 2008/0022758 A1  Jan. 31, 2008

Related U.S. Application Data

(60) Provisional application No. 60/835,056, filed on Aug. 2, 2006.

(30) Foreign Application Priority Data

Jun. 22, 2006  (FR)  .................................. 06 05740

(51) Int. Cl.
*G01N 11/16*  (2006.01)
(52) U.S. Cl. .................... 73/54.39; 73/54.01; 73/54.28; 73/54.37; 73/843
(58) Field of Classification Search ................ 73/54.01, 73/54.03, 54.14, 54.23, 54.28, 54.37, 54.39, 73/843
See application file for complete search history.

(56) References Cited

U.S. PATENT DOCUMENTS

| | | | |
|---|---|---|---|
| 2,752,778 A | | 7/1956 | Edward et al. |
| 3,500,677 A | * | 3/1970 | Broyles et al. ............. 73/54.37 |
| 4,095,461 A | | 6/1978 | Starita |
| 4,154,093 A | * | 5/1979 | Smith et al. ................ 73/54.27 |
| 4,794,788 A | * | 1/1989 | Masters et al. ............. 73/54.27 |
| 4,884,437 A | * | 12/1989 | Constant et al. ............ 73/54.01 |
| 5,253,513 A | * | 10/1993 | Van Arsdale et al. ....... 73/54.41 |
| 5,520,042 A | * | 5/1996 | Garritano et al. ........... 73/54.02 |
| 6,571,610 B1 | * | 6/2003 | Raffer ........................ 73/54.35 |
| 6,681,617 B1 | * | 1/2004 | Putman et al. .............. 73/54.27 |
| 6,681,618 B2 | * | 1/2004 | Hajduk et al. .............. 73/54.37 |
| 6,962,086 B2 | * | 11/2005 | Prescott et al. .................. 73/846 |
| 6,978,662 B2 | * | 12/2005 | Platzek et al. .............. 73/54.42 |
| 7,249,523 B2 | * | 7/2007 | Nickerson ..................... 73/846 |

FOREIGN PATENT DOCUMENTS

| | | |
|---|---|---|
| EP | 1 698 881 A | 9/2006 |
| WO | WO 02/42739 A | 5/2002 |

* cited by examiner

*Primary Examiner*—David A. Rogers
(74) *Attorney, Agent, or Firm*—Cohen Pontani Lieberman & Pavane LLP

(57) ABSTRACT

Device for measuring the rheological properties of a viscoelastic material, formed of an upper rotating plate (10) and of a lower rotating plate (20) which are able to press against the opposite faces of a sample S of the material to be measured. The axes of rotation ($a_1$ $a_1'$ and $a_2$ $a_2'$) of said plates are arranged parallel to one another in a direction perpendicular to the plane formed by the plates, and offset from one another by a distance d. Two independent motors (12, 22) drive respectively the upper plate (10) and the lower plate (20) at the same speed of rotation ω, without giving rise to any angular displacement between the two plates.

12 Claims, 3 Drawing Sheets

ORTHOGONAL RHEOMETER

RELATED APPLICATIONS

This application claims priority from U.S. Provisional Patent Application Ser. No. 60/835,056 filed Aug. 2, 2006 and French Patent Application No. 06/05740 filed Jun. 22, 2006, the contents of both of which are hereby incorporated by reference.

FIELD OF THE INVENTION

The invention relates to a device for measuring the rheological properties of a sample of viscoelastic material, such as rubber.

BACKGROUND OF THE INVENTION

The viscoelastic properties of a material are described by physical parameters such as the viscous modulus (G"), the elastic modulus (G'), or else by the relationship $$\frac{G''}{G'} = Tg\delta,$$

which is the tangent of the angle of offset between stress and deformation when the material is subjected to sinusoidal stress, and which makes it possible inter alia to characterize the phenomena of dissipation inside the material.

There is a wide range of means which make it possible to measure these physical characteristics. The most widespread means are oscillating rheometer, in which the sample to be evaluated is held between two plates, rotatable one respectively to the other. The values of the viscous and elastic modulus results from the measurement of the efforts exerted by the sample upon the axis of rotation, once the mobile plate is oscillating within a slight angular value. These means are known, as example, from publication U.S. Pat. No. 2,752,778, or from publication WO 02/42739. One other means, the physical principles of which have been described by Gent in the Journal Apply of Physics (1960, 11, 165) or by Maxwell and R P Chartoff in the review Trans. Soc. Rheol (1965, 9, 41), is known by the name of orthogonal rheometer. The physical laws of such a rheometer have been developed by way of example by C. W. Macosko and W. M. Davis in the manual dedicated to rheometry which bears the title Rheometry Acta (1974, 13, 814).

An orthogonal rheometer, a block diagram of which is shown in FIGS. 1 and 2, comprises two rotating plates 10 and 20, the planes of which are parallel to one another, and which are spaced apart by a given distance e. The sample E to be measured, of cross section S, is placed between the two plates. The axes of rotation of the two plates, respectively $a_1$ $a_1'$ and $a_2$ $a_2'$, are not collinear, but rather are offset by a distance d in a direction XX' which is perpendicular to said axes of rotation and parallel to the plane of the plates.

The orthogonal rheometer of the prior art, which is described in the aforementioned work by Maxwell and Chartoff, comprises a driving motor which is able to drive the upper plate in rotation at a constant speed ω, the other plate being held by a shaft with the lowest possible friction resistance. This shaft is itself driven in rotation via the sample E, at a speed of rotation equal to ω.

The lateral forces exerted by the sample on the lower plate in the direction XX' and in the direction YY', which is perpendicular to the direction XX' and to the axes of rotation $a_1$ $a_1'$ and $a_2$ $a_2'$, i.e. respectively Fx and Fy, are measured by suitable means and make it possible to calculate the values of G' and of G" at a stress frequency equal to ω.

By considering the value $$\gamma = \frac{d}{e},$$

the following results are obtained:

$$G' = \frac{Fx}{S\gamma}$$

$$G'' = \frac{Fy}{S\gamma}$$

$$Tg\delta = \frac{Fy}{Fx}$$

These equations are valid when the value of γ is sufficiently small, and when the effects associated with the inertia of the plates is ignored.

It will be noted that one of the known advantages of this type of rheometer is that it makes it possible to measure a sample having a cross section of any shape, provided that the value of this cross section is known at the time of measurement.

The publication U.S. Pat. No. 4,095,461 describes an orthogonal rheometer which is based on these principles, in which the upper plate is driven in rotation by a motor mounted on a fixed chassis, and in which the lower plate is mounted on a shaft which has a very low resistance to rotation, and on which the lateral forces Fx and Fy are measured.

The lower shaft is mounted on a platform which is able to move with respect to a fixed chassis, so as to make it possible to move the axis of the lower plate away from the axis of the upper plate by a desired value d in the direction XX'.

However, the type of construction described in the publications mentioned above by way of reference gives rise to stresses which are prejudicial to the quality of the measurement. This is because, with this type of mounting, the sample drives the lower plate in rotation, and a friction torque is created between the movable platform and the lower support, which is associated with the braking torque generated by the bearings of the lower plate.

Moreover, the vertical load Fz which is applied so as to keep the sample E between the faces of the upper plate and the lower plate creates a friction torque which is felt in the sample E, which is then subjected to a parasitic torsional stress. This results in a change in the value of the forces Fx and Fy, which takes the form of an alternating sinusoidal signal (of the same frequency as the rotation frequency ω). Analysis of the measurement signal then requires the use of sensors with a very high pass-band, of a filtering means, and of suitable data processing software.

SUMMARY OF THE INVENTION

One object of the invention is to provide a solution to these problems by making it possible to eliminate the effects associated with the inertia of the plates and the friction torque, so as to improve the precision of the measurement of lateral forces and the calculation of the value of the parameters G' and G" of the sample.

This and other objects are attained in accordance with one aspect of the invention directed to a device for measuring the rheological properties of a material. It is formed of an upper rotating plate and of a lower rotating plate which are able to press against the opposite faces of a sample E of the material to be measured. The axes of rotation of said plates are arranged parallel to one another in a direction perpendicular to the plane formed by the plates, and offset from one another by a distance d. Two independent motors are able to drive respectively the upper plate and the lower plate at the same speed of rotation ω, without giving rise to any angular displacement between the two plates.

This assembly, comprising two motors, makes it possible to overcome the aforementioned disadvantages in that each of the plates is driven in rotation independently of one another. The parasitic forces brought about by the driving of the lower plate by the upper plate through the torque transmitted by the sample are eliminated, and the measured forces Fx and Fy are closer to the actual rheological values.

The holding force Fz which is designed to hold the sample can then be varied according to the holding requirements of the sample E, without this having any effect on the rotation of the plates and on the forces Fx and Fy.

The person skilled in the art will understand that, in order for the measurement to be valid, the two plates should rotate strictly at the same speed. In other words, at each time interval, the two plates should undergo an identical angular deviation in order to prevent any rotation offset between the two plates, so as not to generate any torsional torque inside the sample.

This performance is achieved by the use of motors of the stepping motor type, in which the control signals are absolutely synchronous.

BRIEF DESCRIPTION OF THE DRAWINGS

The following description is based on FIGS. 1 to 4, and makes it possible to illustrate a preferred embodiment of the invention in which.

DETAILED DESCRIPTION OF THE DRAWINGS

Figure 1:
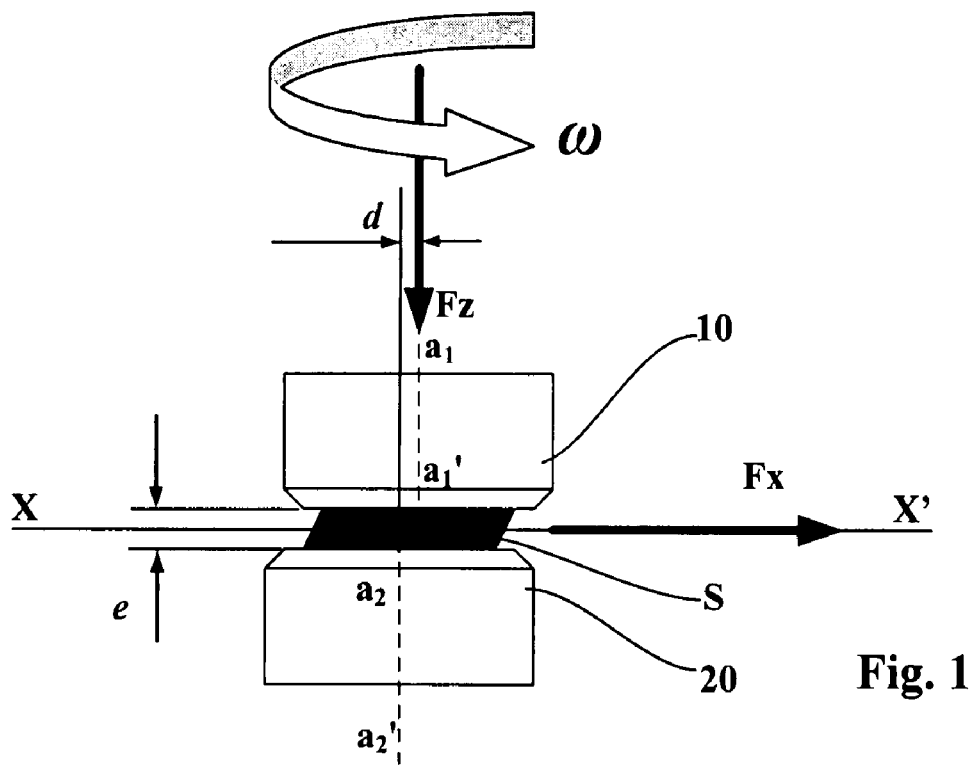
FIGS. 1 and 2 show, as already mentioned in the paragraphs above, block diagrams of an orthogonal rheometer.
Figure 2:
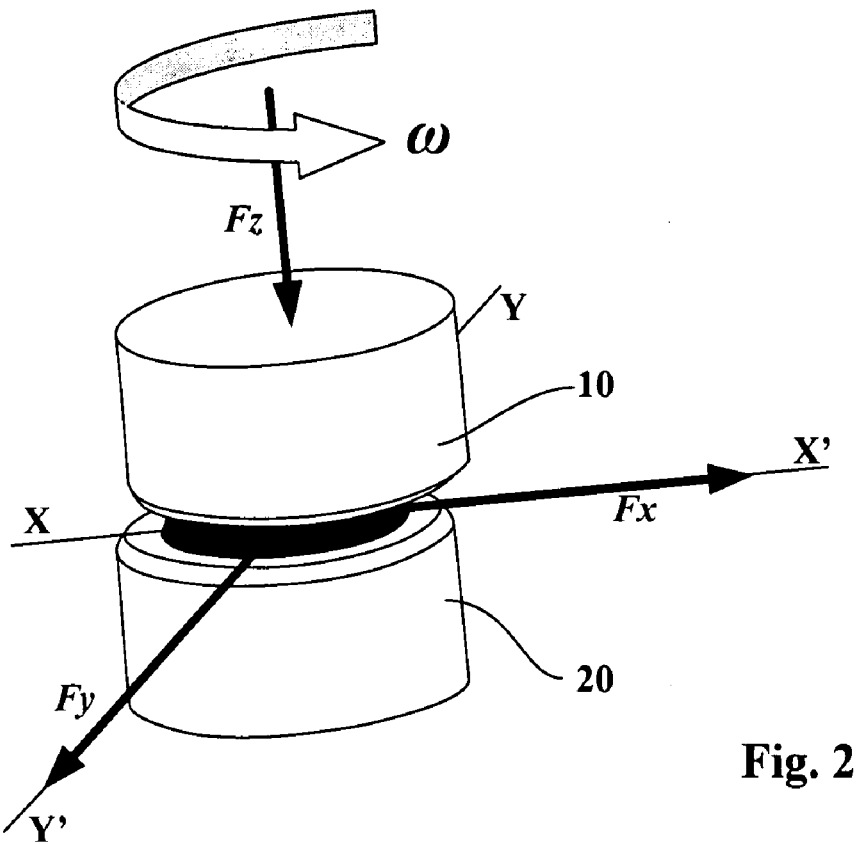
Figure 3:
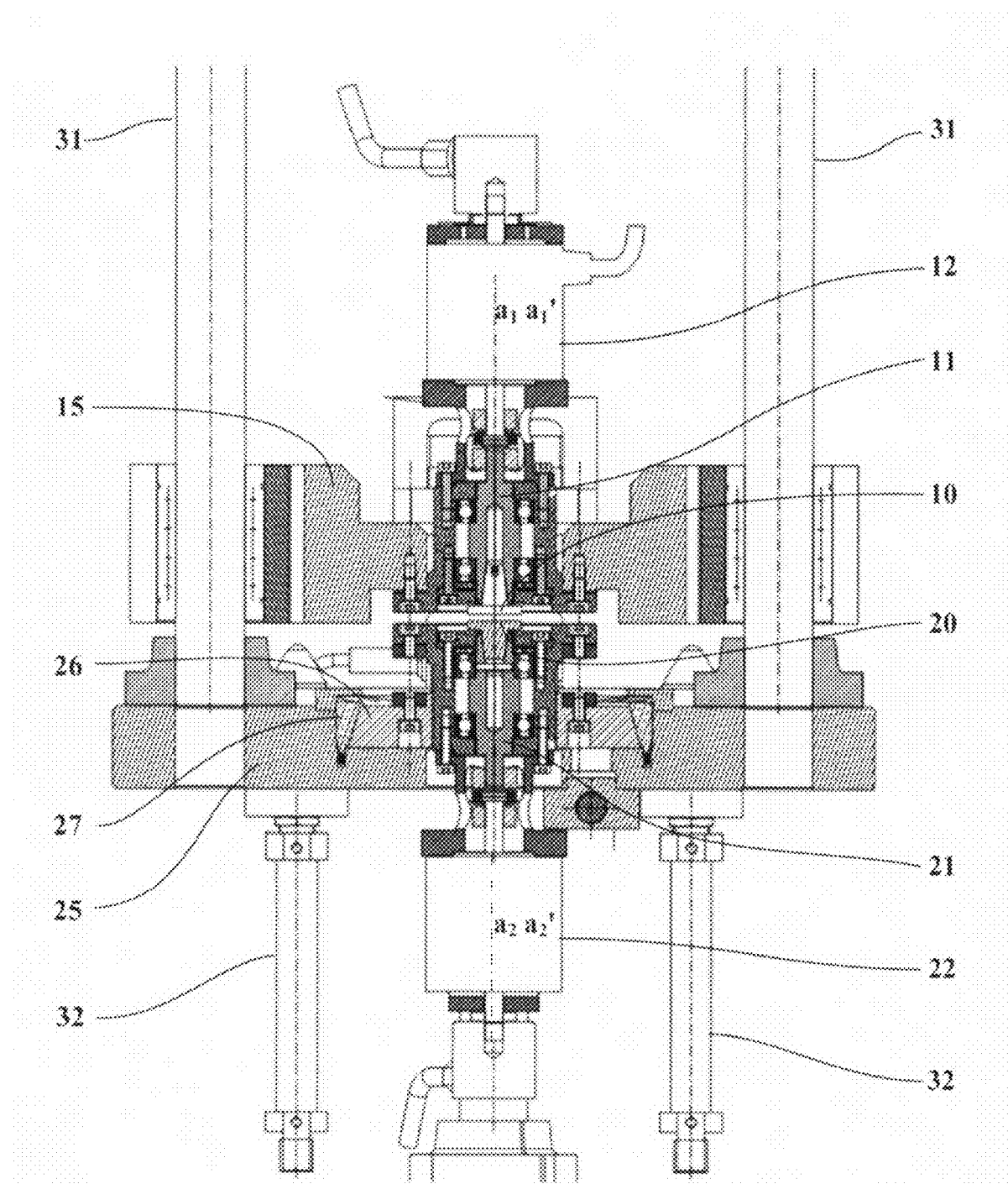
FIG. 3 shows a view in cross section of one example of mounting a rheometer according to the invention.

FIG. 3 shows a measurement device according to an embodiment of the invention, in which there can be seen the upper plate 10 and the lower plate 20, which are arranged in planes parallel to one another and which are designed to hold the sample E of material to be measured. These plates are borne by rotary bearings, respectively 11 and 21, which are driven in rotation by electric motors, respectively 12 and 22.

It proves to be particularly advantageous to align the output rotor of the motor, the rotary bearing and the axis of rotation of the plate along one and the same axis, i.e. respectively $a_1 a_1'$ for the upper assembly and $a_2 a_2'$ for the lower assembly.

The rotary bearings 11 and 21 are mounted respectively on an upper platform 15 and a lower platform 26.

The upper platform 15 slides on uprights 31 in a vertical direction, perpendicular to the plane formed by the plate 10. In the raised position, it is possible to access the plates so as to insert or remove a sample. In the measuring position, and in the presence of a sample, the plates are brought together so as to exert a predefined holding pressure on the opposite faces of the sample E, so that the plates are positioned at a distance e from one another. It will be noted that this distance e, which corresponds essentially to the thickness of the sample E, does not need to be calibrated and can be evaluated by a suitable means at the time of measurement.

In practice, care will be taken to prevent any sliding of the faces of the sample with respect to the plates, by carefully selecting the mode of machining the surfaces of the plates that are in contact with the opposite faces of the sample. By way of example, a cutting of the surface of the plates comprising diamond-cut grooves gives good results regardless of the modulus of the materials used. These precautions make it possible to reduce the value of the force Fy which is applied to the sample by the plates in the vertical direction.

The lower platform 26 is mounted on the chassis 25 so as to be able to be displaced horizontally along an axis XX' (not shown). By displacing the lower platform 26 in this direction with respect to the upper platform, it is possible to create an offset d between the axes $a_1 a_1'$ and $a_2 a_2'$. This translational movement can be controlled by means of a mechanical cam generator 27, or else by means of a micrometer table. The chassis 25 is itself mounted on supports 32 so as to free the lower space which is required to accommodate the motor and the lower bearing.

As has been seen above, the control of the motors is very important so as to ensure that the two plates rotate strictly at the same speed. FIG. 5 shows the block diagram of a control means which makes it possible to obtain this performance.

In order to ensure perfectly synchronous rotation of the motors 12 and 22, motors known as stepping motors will preferably be selected.

This is because this type of technology makes it possible to control the motors simultaneously without having to measure a difference with respect to a tracking value, which would have the effect of generating an angular displacement between the two plates.

These motors are supplied by control modules C1 and C2 which are controlled by pulses. Each pulse gives rise to a rotation through one step which is determined at the output shaft of the motor. In order to ensure a high level of precision, motors of a type which give rise to a rotation of less than 1° per step or per pulse will be selected. In practice, good results have been obtained with motors carrying out 500 steps per revolution. If one revolution represents an angle of 360°, this is the equivalent of a rotation through an angle of 0.72° per pulse.

By virtue of a combined supply to the coils, it is also possible to control the motor to $\frac{1}{10}^{th}$ of a step, which increases the control precision by a factor of 10.

Similarly, it is important that the two plates can rotate together in a perfectly synchronous manner so as to avoid causing any parasitic torsion of the sample. To this end, the same pulse trains are sent to each of the control modules C1 and C2, by controlling these two modules by means of an oscillator O, the oscillation frequency of which is modulated as a function of the desired speed of rotation ω.

In this way, it is possible to make the two plates rotate at the same speed by operating in such a way that the two plates carry out strictly the same angular displacement during the rotation. Thus, at any given moment, the total rotation offset between the two plates is less than or equal to an angle of 0.25°. This means that the torsional deformation imposed on the sample by the plates as a result of a rotation offset between the two plates does not at any time exceed an angle of 0.25°, which can be considered negligible. In practice, it is possible to obtain values of less than an angle of 0.2°.

One particular problem that has to be solved concerns the start-up and stoppage configurations, during which the torques are higher than the torques that are required in the steady state. To this end, motors will be selected which have a nominal power that is several orders of magnitude higher than the power required to set the plates in rotation when a sample is placed in the rheometer in order to be measured.

In practice, motors will be selected which have a power that is more than 3 times higher than the power required to make the plates rotate in the presence of a sample. The speed of rotation ω of the plates can thus vary from a stopped position to a steady-state position without giving rise to any angular offset between the two plates.

It is also possible to control the rotation offset between the two plates during this start-up phase by ensuring that the mechanical assemblies of the two plates are substantially identical. Thus, by selecting motors 12 and 22 of the same model and of essentially equal weight, along with plates 10, 20 and bearings 11 and 21 that are substantially identical, it is possible to obtain assemblies of very similar weight and inertia. In this way, all the control anomalies have substantially the same effect on each of the plates.

The speed ω at which the measurement is carried out is stabilized at the level representative of the stress frequencies of the material. In practice, it is possible to carry out measurements at speeds which may vary from several revolutions per minute up to 2500 rpm or even 3000 rpm in the case of materials which are subjected to stress at a very high frequency.

Figure 4:
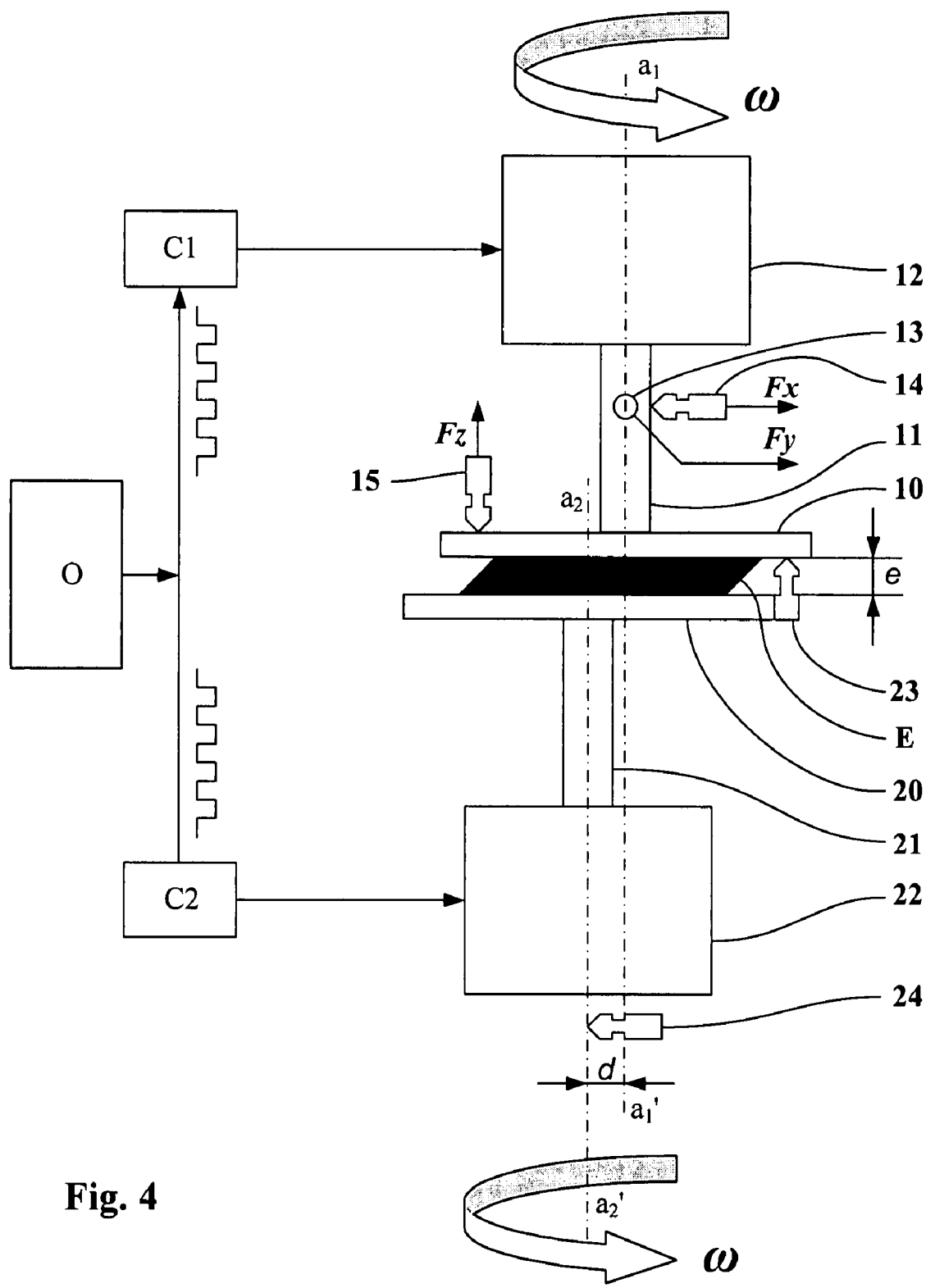
FIG. 4 shows a block diagram of the control and measuring elements of an orthogonal rheometer according to the invention.

As shown in FIG. 4, one of the axes is designed to receive the means for measuring the forces Fx and Fy which are generated by the sample in reaction to the imposed deformations to which it is subjected. These measurement means are usually strain gauges. The measurement means may be provided on the axis of either the upper plate or the lower plate.

It is also possible to provide one of the plates with a gauge which makes it possible to estimate the force applied to the sample in the vertical direction, and which corresponds to the holding force that is required in order to hold said sample during the measurement.

Knowledge of the values of the parameters e and d is obtained at the time of measurement via a means (23) which makes it possible to evaluate the distance between the two plates, and a means (24) which makes it possible to evaluate the offset between the axes $a_1 a_1'$ and $a_2 a_2'$.

The values of the parameters e and d are thus provided, which are necessary in order to calculate the value γ. In practice, depending on the thickness e of the sample E, the value d of the offset between the axes is adjusted so as to obtain a sufficiently small value for the relationship $$\gamma = \frac{d}{e}.$$

The values of G' and of G" are determined by calculus, using algorithms and means which are known and which do not form part of the subject matter of the present description.

The sample must be prepared with care. This is because it is important that the sample E has a constant thickness over its entire cross section. The value of the cross section S of the sample may be determined with precision by means of a digital camera.

Given the measurement precision which is obtained with a rheometer according to the invention, it is thus possible to measure samples which have a thickness of only a few tenths of a mm, the shape of the cross section S and the thickness of which do not need to be calibrated beforehand.

Similarly, when it is desired to analyse viscoelastic materials such as rubbers, it becomes possible to carry out measurements on the non-vulcanized material without the latter deforming under the effects of its high level of plasticity, due to the low holding force that is required and also the extreme rapidity of the measurement. This is because a few revolutions may be sufficient to obtain meaningful values for the elastic and viscous moduli of the material.

The invention claimed is:

1. A device for measuring the rheological properties of a viscoelastic material, comprising:
    an upper rotating plate (10) and a lower rotating plate (20) which are able to press against the opposite faces of a sample E of the material to be measured, the axes of rotation ($a_1 a_1'$ and $a_2 a_2'$) of said plates being arranged parallel to one another in a direction perpendicular to the plane formed by the plates, and offset from one another by a distance d; and
    two independent motors (12, 22) which are able to drive respectively the upper plate (10) and the lower plate (20) at the same speed of rotation ω, without giving rise to any angular displacement between the two plates.

2. The measurement device according to claim 1, wherein the power of the motors (12, 22) is more than 3 times higher than the power necessary to set the plates in rotation when a sample S is placed on said device in order to be measured.

3. The measurement device according to claim 1, wherein the axis of rotation of the stepping motors ($a_1 a_1'$ and $a_2 a_2'$) is coincident with the axis of rotation of the plate (10, 20) to which it is connected.

4. The measurement device according to claim 1, comprising a means (23) for measuring the distance e between the two plates.

5. The measurement device according to claim 1, wherein one of the axes of rotation ($a_1 a_1'$) is equipped with means (13, 14) for detecting the lateral forces Fx and Fy generated by the sample S on the plates (10, 20) in two directions XX' and YY' parallel to the plane of the plates and perpendicular to one another, in reaction to the deformations imposed on said sample S, when said sample S is placed on said device in order to be measured.

6. The measurement device according to claim 5, wherein the means (13, 14) for detecting the forces Fx and Fy are strain gauges.

7. The measurement device according to claim 1, wherein one of the plates (20) is provided with translation means (26, 27) for varying the offset d between the axes ($a_1 a_1'$ and $a_2 a_2'$) of the plates (10, 20).

8. The measurement device according to claim 7, comprising a means (24) for measuring the offset d between the axes ($a_1 a_1'$ and $a_2 a_2'$) of the plates (10, 20).

9. The measurement device according to claim 1, wherein the motors (12, 22) are stepping motors, with each of the stepping motors (12, 22) being controlled by a control module (C1, C2).

10. The measurement device according to claim 9, wherein the control modules (C1, C2) make the plates (10, 20) rotate through an angle of less than 1° per step.

11. The measurement device according to claim 10, wherein each said control module (C1, C2) generates a pulse train, said pulse trains being exactly synchronous, so that the total rotation offset between the two plates (10, 20) is at any moment less than an angle of 0.25°.

12. The measurement device according to claim 11, wherein the control modules (C1, C2) of the stepping motors (12, 22) are themselves controlled by one and the same oscillator (O) which is able to send the same pulse trains to each of said control modules.

* * * * *